United States Patent [19]

Reid et al.

[11] Patent Number: 4,539,292

[45] Date of Patent: Sep. 3, 1985

[54] IMMUNOASSAY TECHNIQUE FOR SPECIFIC IMMUNOGLOBULIN E

[76] Inventors: Michael J. Reid, 3404 Royal Ct., Napa, Calif. 94558; J. Michael Kwasnicki, 113 Richard Pl., Vacaville, Calif. 95688; Nai-Kong V. Cheung, 2101 Adelbert Rd., Cleveland, Ohio 44106

[21] Appl. No.: 454,219

[22] Filed: Dec. 29, 1982

[51] Int. Cl.³ .......................................... G01N 33/54
[52] U.S. Cl. ........................................ 435/7; 436/513; 436/548; 436/825
[58] Field of Search .................... 435/7; 436/513, 548, 436/825

[56] References Cited

U.S. PATENT DOCUMENTS

| | | | |
|---|---|---|---|
| 3,188,181 | 6/1965 | Peterson et al. | 141/130 |
| 4,092,116 | 5/1978 | Giaever | 436/525 |
| 4,104,026 | 8/1978 | Brooker et al. | 436/541 |
| 4,207,075 | 6/1980 | Liburdy | 436/528 |
| 4,243,651 | 1/1981 | Nalebuff | 436/513 X |
| 4,376,110 | 3/1983 | David et al. | 436/548 X |
| 4,430,437 | 2/1984 | Hampar et al. | 436/548 |
| 4,434,227 | 2/1984 | Unger | 436/513 X |
| 4,455,381 | 6/1984 | Magnusson et al. | 436/518 X |

FOREIGN PATENT DOCUMENTS 0106324  4/1984  European Pat. Off. ................ 435/7

OTHER PUBLICATIONS

Majid et al., An Immunoperoxidase Assay for Serum Ragweed–Specific IgE, Annals of Allergy, 42, 231–235 (1979).
Reid et al., Microtiter Solid Phase Radioimmunoassay for Total Serum IgE, Annals of Allergy, 46, 3, 132–136 (1981).
Reid et al., Microtiter Solid-Phase Radioimmunoassay for Specific Immunoglobulin E, J. Allergy Clin. Immunology 67, 4, 263–271 (1981).

Primary Examiner—Sidney Marantz
Assistant Examiner—Shawn P. Foley
Attorney, Agent, or Firm—Donald J. Singer; William J. O'Brien

[57] ABSTRACT

Using monoclonal mouse anti-human IgE antibodies, the microtiter solid phase radioimmunoassay (MSPRIA) and the enzyme-linked immunoabsorbent assay (EILSA) were modified to quantitatively measure honeybee venom (HBV) and perennial rye grass (PRG) specific immunoglobulin E (sIgE). By using a novel dilution, serial transfer and cummulative counting technique, the inhibiting and interfering effects of specific immunoglobulin G (sIgG) in the assay of (sIgE) can be reduced and the quantitative determination of (sIgE) accomplished with precision and reliability.

5 Claims, 2 Drawing Figures

IMMUNOASSAY TECHNIQUE FOR SPECIFIC IMMUNOGLOBULIN E

STATEMENT OF GOVERNMENT INTEREST

The invention described herein may be manufactured and used by or for the Government for governmental purposes without the payment of any royalty thereon.

FIELD OF THE INVENTION

This invention relates to an immunoassay technique for quantitively measuring specific immunoglogulin E. More particularly, this invention concerns itself with a method for reducing the interfering effects of specific immunoglobulin G when attempting to determine specific immunoglobulin E in an immunoassay of blood sera.

BACKGROUND OF THE INVENTION

A continuing research effort is being maintained in and attempt to understand the role played by immunoglobulin antibodies in the mechanism of the antigen-antibody immunological reaction. The antigen-antibody reaction serves as a defense against the effects produced when a host body, human or animal, is invaded by microorganisms or other foreign bodies which cause infections, diseases or toxic reactions. This reaction is also relied upon to detect the presence or absence of either antigens or antibodies in human or animal sera. The presence of antigen molecules, such as honeybee venom, in a host body induces the production of an antibody called immunoglobulin. The antibody molecule has reactive sites which are capable of reacting with reactive sites on the antigen molecule to produce an immunological complex. The critical factor in the antigen-antibody reaction is that the antibody will combine specifically with the induced antigen.

The three major classes of immunoglobulin antibodies in human serum are immunoglobulin G (IgG), immunoglobulin A (IgA) and immunoglobulin M (IgM). Two other classes of distinct immunoglobulins are immunoglobulin E (IgE) and immunoglobulin D (IgD). IgG is the most abundant antibody in human serum and consists of two pairs of polypeptide chains linked by disulfide bonds. The peptide chains are oriented in the shape of the letter "Y". The reactive sites on the molecule are represented by the ends of the two arms of the Y-oriented antibody.

IgA is the second most abundant immunoglobulin in human serum while IgM is the largest immunoglobulin and the first to appear during primary immune response. IgD and IgE are present in only minor amounts in normal human serum. IgE functions as a mediator of hypersensitivity such as the allergic reaction to honeybee venom (HBV). After binding to the HBV antigen, it causes the release of histamine and its attendant problems. Therefore, the determination of IgE plays an important part in the diagnosis of the atopic state and for measuring response to treatment. As a consequence, numerous methods have been suggested for quantitating serum IgE levels. Among some of the more important methods for determining IgE levels are radial immunodiffusion, double antibody precipitation, a variety of microtiter solid phase radioimmunoassays (MSPRIA) using various coupled bodies, and an enzyme-linked immunosorbent assay technique (ELISA).

In the (MSPRIA) technique for determining specific IgE, the assay is carried out in flexible polyvinyl chloride "u" microtiter test plates by sequentially incubating antigen, albumin, test sera, and finally radiolabeled rabbit or goat antihuman IgE. Wells are cut free of the test plate with a hot wire-cutting apparatus and counted individually in a gamma counter. The amount of radioactivity bound is then proportioned to the amount of specific IgE in the serum. The MSPRIA technique is antigen and antibody specific. Rye-specific IgE levels assayed with the MSPRIA technique correlated with quantitative end point titration skin tests using perennial rye antigen. The rye-specific IgE levels assayed by MSPRIA also correlated with those assayed by RAST with a correlation coefficient of 0.95. The MSPRIA is well suited for mass screening and represents a useful method for measuring specific IgE. The (ELISA) assay technique for determining specific IgG is similar to the (MSPRIA) technique but with some differences. In this technique the assay is performed in polyvinyl chloride "u" microtiter plates having a series of test wells in which an antigen is incubated and absorbed on the walls of the polyvinyl chloride test wells. The antigen is sequentially overlaid with human albumin serum (HSA), unknown test serum diluted in 10% normal goat serum (NGS) and peroxidase-labeled goat or rabbit antihuman IgG in (NGS). O-Phenylenediamine (OPD) was used as a substrate. After incubation, the color reaction from the (OPD) was stopped and read on a spectrophotometer. A quantitation of the specific IgG was made by comparison to a known reference curve having arbitrarily assigned quantities of the specific IgG.

The (MSPRIA) and (ELISA) techniques have proved successful since the antigens or antibodies can absorb to a microtiter polyvinyl plate without the need of chemical modification for bonding. In addition, the plastic plates are of convenient size for handling and washing procedures. Unfortunately, most of these tests have not been able to measure IgE quantitatively according to a known reference and are expressed semi-quantitatively. There is also considerable interference from IgG when making a determination for IgE. This makes test results less reliable and it makes it difficult to compare one assay to another.

With the present invention, however, it has been found that modifying the (MSPRIA) or (ELISA) assay technique, in accordance with the techniques of this invention, reduces interference from specific IgG, a factor of particular importance to patients on immunotherapy; and is quantitative and referenced to a known and available standard (the NIH IgE reference). The modifications of this invention over that of the conventional (MSPRIA) AND (ELISA) techniques comprise the use of a monoclonal mouse anti-human IgE antibody which is labeled by using radioactive $^{125}$I in the case of the (MSPRIA) technique; and with peroxidase enzyme in the case of the (ELSIA) technique. Another basic difference resides in the fact that the supernatant fluid in the test well is serially transferred to additional test wells a sufficient number of times to materially and significantly reduce interference from the effects of IgG.

The modifications of the conventional (MSPRIA) and (ELISA) assay techniques as conceived by this invention, that is the serial transfer of supernatant fluid and the use of monoclonal mouse antihuman IgE (rather than affinity-column purified anti-IgE) are novel and provide the means for allowing very precise measurements and sensitivity of undiluted or low dilutions of serum samples.

SUMMARY OF THE INVENTION

In accordance with the present invention, it has been found that novel modifications of the conventional (MSPRIA) and (ELISA) immunological assay techniques provide a solution to the problems of quantitating (IgE) in human test sera with the high degree of accuracy and reliability required for the diagnosis and management of allergic diseases.

Using monoclonal mouse anti-human IgE antibody, the microtiter solid phase radioimmunoassay (MSPRIA) and the enzyme-linked immunosorbent assay (ELISA) were modified to quantitatively measure an antigen specific IgE such as honey bee venom (HBV) or perennial rye grass (PRG) specific IgE. Non-linear (and therefore non-quantifiable) dilution curves are associated with high specific IgG content. However, by dilution, serial transfer and assay of the IgE, inhibition by the specific IgG can be reduced. By performing serial transfers measuring specific IgE until the accumulated counts of absorbance plateaued, the specific IgE can be quantitated with a high degree of accuracy. For example, the technique of this invention can be made specific for any immunogenic molecule. Simplicity, reliability, accuracy and rapidity of the procedures, as well as its potential versatility, make it a desirable adjunct to existing methodologies.

Accordingly, the primary object of this invention is to provide a simple and accurate technique for quantitating specific IgE.

Another object of this invention is to provide an immunoassay technique that severely restricts the interfering effects of IgG when determining IgE in a test serum.

Still another object of this invention is to provide a method that utilizes monoclonal mouse antihuman IgE as a diagnostic tool in immunoassay techniques.

The above and still other objects and advantages of the present invention will be more readily understood upon consideration of the following detailed description thereof when viewed in conjunction with the accompanying drawing.

DETAILED DESCRIPTION OF THE PREFERRED EMBODIMENT OF THE INVENTION

Pursuant to the above-defined objects, the present invention involves the use of monoclonal mouse anti-human IgE antibodies in a modified microtiter solid phase radioimmunoassay (MSPRIA) or an enzyme-linked immunosorbent assay (ELISA) in order to quantitatively measure antigen-specific immunoglobulin E (s IgE) in human test sera.

The continuing research effort to understand the role of IgE in the Pathophysiology of disease has produced a number of methods for the in vitro detection of this antibody. The most successful of these are variations of the radioallergosorbent test (RAST). These tests have correlated well with allergic symptomatology, allergy skin tests, bronchial and nasal provocation tests, and leukocyte histamine release. However, a number of technical problems have prevented wide acceptance of this technique in clinical medicine. It is expensive and relatively laborious to perform. Also, most methods require chemical binding of the antigen to the solid phase, a step that poses the possibility of protein denaturation.

A solution of these problems would permit a much wider use of in vitro quantification of specific IgE with a resultant standardization of diagnostic and therapeutic techniques. In an attempt to provide a solution, a microtiter solid phase radioimmunoassay technique (MSPRIA) and an enzyme-linked immunosorbent assay technique (ELISA) were developed. Unfortunately, the problems referred to above were not completely solved because of the interfering effects of IgG encountered when testing human sera samples for specific IgE. With the present invention, however, these problems have been overcome by modifying these (MSPRIA) and (ELISA) techniques to quantitatively measure, with accuracy, specific IgE such as honeybee venom specific IgE (HBV-s IgE) and perennial rye grass specific IgE (PRG-s IgE).

Figure 1:
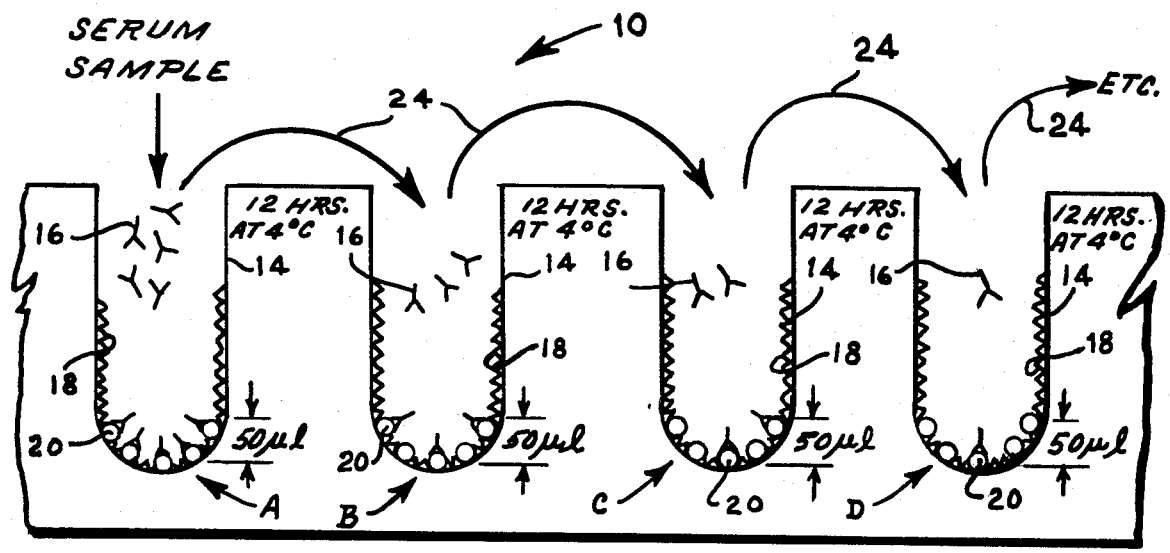
FIGS. 1 and 2 illustrate schematically a polyvinyl chloride microtiter test plate having four test wells. The wells of FIG. 2 are the same wells as shown in FIG. 1 at a later stage in the technique of this invention.
Figure 2:
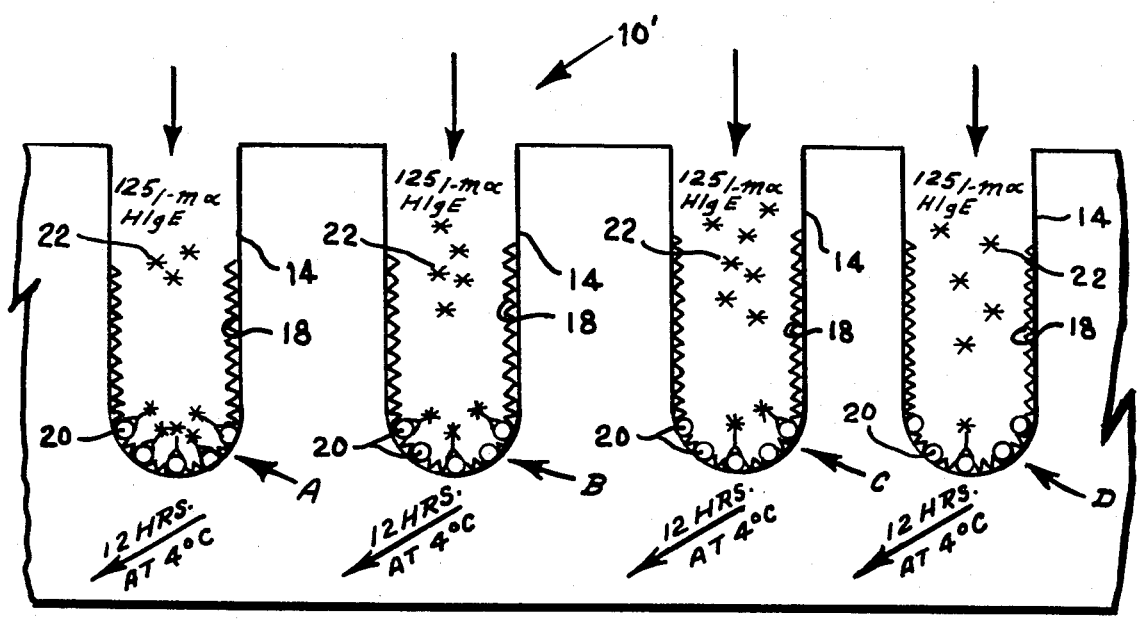

In order to illustrate the present invention with greater specificity and demonstrate how the present invention is carried into effect, reference is made to FIGS. 1 and 2 of the drawing. FIG. 1 discloses a flexible polyvinyl chloride microtiter test plate 10 having four test wells A, B, C and D. FIG. 2 discloses the same test plate, designated herein as 10 prime, with the same four test wells A, B, C and D at a later stage in the assay technique of this invention. Dialysed honeybee venom antigen 20, in the amount of 0.05 ml, and diluted in phosphate buffered saline (PBS), was placed in Well A of the polyvinyl chloride microtiter test plate 10. The plate was incubated for 60 minutes at 37° C. The antigen 20 was aspirated and 0.1 ml of 0.1% globulin-free human serum albumin (HSA) 18 was add to Well A and incubated for 60 minutes at 4° C. then washed three times with (PBS) and then dried. Next, 0.05 ml of an unknown test serum 16, containing IgG, IgE and other proteins, was added to Well A and incubated at 4° C. for 12 to 24 hours. The resulting supernatant fluid remaining in Well A was aspirated and then transferred to Well B, to which had been previously added and incubated the same antigen and globulin-free (HSA) in the same manner as was added to Well A. Well B, with the test serum or supernatant fluid from Well A, was then incubated from 12 to 14 hours at 4° C. The procedure utilized with respect to Well A and Well B was repeated by aspirating the remaining supernatant fluid in Well B and transferring it to the next well, in this case Well C and then Well D, as indicated by the arrows 24. From a practical standpoint, four transfers, as shown in FIG. 1, produces excellent results although, as stated heretofore, a lesser or greater number of serial transfers may be resorted to, if desired. After the final transfer and incubation has taken place, the remaining supernatant fluid is aspirated from the final well and then discarded.

In the next step of the novel assay technique of this invention, as shown in FIG. 2, all the Wells are washed as before with (PBS) and then 0.05 ml of radioactive $^{125}I$ labeled monoclonal mouse anti-human immunoglobulin E ($^{125}I$-m HIgE) was added to each of Wells A, B, C, and D of test plate 10 prime. The test plate 10 prime was incubated 12 to 24 hours at 4° C. After incubation, the Wells A, B, C, and D were each washed three times with (PBS) to remove any excess solution remaining in the Wells. The wells were dried and then cut from the test plate 10 prime with a hot wire apparatus, placed in counting vials, and counted in a Beckman gamma counter. The individual count from each of the four wells A, B, C and D were added together to obtain a cumulative number. This was compared to a calibration curve constructed from a standard with known amounts of (sIgE). The (sIgE) contents were calculated in international units/ml or ng/ml by interpolation from the reference curve. In this fashion, all the (sIgE) in the serum test sample was detected regardless of interfering IgG.

In using the radiolabeled monoclonal mouse anti-human IgE antibody modified (MSPRIA) technique of this invention, 24 human subjects with a history of systemic reaction to honeybee stings and 11 control volunteers with a sensitivity of 0.1 WHO-IgE unit (243pg) ml, were tested by measuring honeybee venom specific IgE (HBV-sIgE).

HBV specific IgE determined by the MSPRIA and RAST correlated with skin test and point titrations ($r=0.89$. p 0.001 and $r=0.9$, p 0.001, respectively and with each other ($r=0.89$. p 0.001). Among the 24 patients, 71% were skin test positive; 67% were MSPRIA and 67% were RAST positive. Agreement between the skin test and the MSPRIA was 79; and 88% between the RAST and skin test. Although the amount of solid phase HBV was limited, interference by specific IgG could be minimized. When serum was diluted such that HBV-specific IgG was reduced from 50 to 6 ng/ml, the percent interference was reduced from 75% to $\leq 15\%$. Moreover, by twice repeated assaying of the supernatants, interference could be further reduced by 40%. With such modifications, the MSPRIA correlated with the skin test end point titration ($r=0.9$, p 0.001) and agreed with skin tests in 88%. Furthermore, 83% of the 24 patients were now MSPRIA (+). It is obvious that the interference of IgG antibodies in antigen-limited MSPRIA systems for specific IgE are overcome by serum dilution and repeated assay of the supernatant when using the monoclonal mouse anti-human IgE antibody technique of this invention.

The method of this invention including the serial transfer of supernatant and the use of monoclonal mouse anti-human IgE antibodies is equally applicable in modifying the enzyme-linked immunosorbent assay (ELISA) technique which can also be utilized to measure specific IgE content such as (HBV) and (PRG) specific IgE. The basic modification of the (ELISA) technique is the same as the modified MSPRIA with the following alternate modifications: 0.1 ml volumes are sued except for the HSA which is 0.2 ml. The wells are washed with PBS containing 0.05% tween 20. Following the test serum incubation, 0.1 ml of unlabeled monoclonal mouse anti-IgE 2.5 mcg/ml is incubated for 3 hours. This is aspirated and the wells are washed 3 times in PBS-tween and dried. Then affinity column purified goat anti-mouse antibody with peroxidase enzyme diluted 1/3000 in 10% normal goat serum is added to each well and incubated 16 to 24 hours at 4° C. This is aspirated and washed 3 times in PBS-tween. At this point 0.01 ml substrate (O-phenylenediamine) at 0.5 mg/ml in citrate buffer is added to each well and a color reaction is produced. This is stopped with 0.150 ml $NH_2SO_4$, diluted 1/10 in 0.1 $NH_2SO_4$ and optical density is read in a spectrophotometer. The optical density of the antigen wells is reported. A standard curve is used to calculate IgE as described above.

As can be seen from the above, the techniques relied upon to modify the conventional (MSPRIA) technique have been adapted to the (EILSA) technique. The antigen, either (HBV) or (PBS), is absorbed to the wells of the polyvinyl microtiter plates and is consecutively overlaid with human serum albumin, unknown serum, monoclonal mouse anti-IgE, and enzyme labeled goat anti-mouse IgG. In the presence of ineterfering IgG, sera are transferred to fresh wells using 8 to 24 hour incubations. The wells are developed by adding substrate, stopped, and the optical density (OD) read on a spectrophotometer. The optical density of the antigen containing wells is accumulated. Results are obtained by interpolating from a reference curve of a serum standardized by assaying in parallel with the NIAID total IgE standard. Non-specific background is reduced to $<2\%$ allowing the use of full strength sera with increasing sensitivity. Correlation with MSPRIA was $r=0.929$, $p<0.001$, $n=32$. Comparison with prick skin tests for 9 antigens produced concordances of 77 to 100%, chi-square $p<0.01$ or better.

From a consideration of the above, it can be seen that the modified immunological assay technique of this invention, including the use of monoclonal mouse anti-human IgE antibodies, rather than the use of affinity-column purified anti IgE as in the past, provides a technique for measuring (sIgE) that significantly improves precision and sensitivity. The resulting assay is precise, sensitive, simple, reliable, quantitative and, in the case of the modified (EILSA) technique, avoids the hazards of radioimmunoassays.

Although the present invention is concerned primarily with determining (sIgE) in blood sera, it should be understood that it can be made specific for any macromolecule against which antisera can be used. Also, it should be further understood, that while the present invention has been described by reference to specific embodiments thereof, various alterations and modifications of the invention may be resorted to and that all such modifications as fall within the scope of the appended claims are intended to be included therein.

What is claimed is:

1. A method for the quantitative determination of immunoglobulin E in a blood serum test sample which comprises the steps of:
   (A) introducing into a polyvinyl chloride test well and incubating an immunologically reactive, specific antigen for about 60 minutes at about 37° C. to effect the absorption of said antigen on the wall of said test well;
   (B) aspirating said specific antigen;
   (C) introducing into said test well and incubating a globulin-free human serum albumin for about 60 minutes at about 4° C.;
   (D) washing and drying said test well;
   (E) introducing into said dry test well and incubating a blood serum test sample for from about 12 to 24 hours at about 4° C. to produce a blood serum supernatant fluid;
   (F) serially transferring and incubating for from about 12 to 14 hours at about 4° C. said supernatant fluid to a succeeding polyvinyl chloride test well previously subjected to steps (A) to (D);
   (G) continuing to serially transfer and incubate sequentially the said supernatant fluid to a pre-determined number of succeeding test wells each of which was previously subjected to steps (A) to (D);
(H) discarding said final supernatant fluid;
(I) introducing into each of said predetermined number of said test wells and incubating for from about 12 to 24 hours at about 4° C. a labeled, monoclonal, mouse, anti-human, immunoglobulin E antibody;
(J) quantitatively measuring and assaying the amount of specific immunoglobulin E in each of said predetermined number of test wells to provide a cumulative total content of specific immunologlobulin E in said blood serum test sample.

2. A method in accordance with claim 1 wherein said labeled monoclonal, mouse, anti-human, immunoglobulin E antibody is radioactively-labeled for assay purposes.

3. A method in accordance with claim 1 wherein said labeled monoclonal, mouse, anti-human, immunoglobulin E antibody is enzyme-labeled for assay purposes.

4. A method in accordance with claim 1 wherein said specific antigen is honeybee venom.

5. A method in accordance with claim 1 and further including the step of introducing an affinity column purified, goat, anti-mouse, antibody into each of said incubated, unlabeled, monoclonal, mouse, antihuman, immunoglobulin E antibody containing test walls and incubating said goat anti-mouse antibody for about 16 to 24 hours at about 4° C.

* * * * *